(12) United States Patent
Williams et al.

(10) Patent No.: US 9,724,505 B2
(45) Date of Patent: Aug. 8, 2017

(54) COUPLING FOR MEDICAL FLUIDS

(71) Applicant: Applied Medical Technology, Inc., Brecksville, OH (US)

(72) Inventors: Derek M. Williams, Cuyahoga Falls, OH (US); Grant W. Phillips, Richfield, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 112 days.

(21) Appl. No.: 14/641,970

(22) Filed: Mar. 9, 2015

(65) Prior Publication Data
US 2015/0238750 A1    Aug. 27, 2015

Related U.S. Application Data

(63) Continuation of application No. 13/192,630, filed on Jul. 28, 2011, now Pat. No. 8,974,437.

(51) Int. Cl.
*A61M 39/10* (2006.01)
*A61M 39/22* (2006.01)
(Continued)

(52) U.S. Cl.
CPC ............ *A61M 39/22* (2013.01); *A61M 39/10* (2013.01); *A61M 39/1011* (2013.01);
(Continued)

(58) Field of Classification Search
CPC .. A61M 2039/1077; A61M 2039/2426; A61M 2039/2433; A61M 39/10; A61M 39/26; A61M 2039/1088
See application file for complete search history.

(56) References Cited

U.S. PATENT DOCUMENTS 3,628,813 A * 12/1971 Lee, Jr. ............... A61M 1/3653
285/120.1
4,511,359 A * 4/1985 Vaillancourt ......... A61M 39/14
285/3
(Continued)

FOREIGN PATENT DOCUMENTS

EP      0795342 A2    9/1997
WO      9006151 A1    6/1990
(Continued)

OTHER PUBLICATIONS

Watson, Christopher M., M.D. and Sawyer, Robert G., M.D., Break-aWay Percutaneous Endoscopic (BW-PEG) Tube, Patent Foundation, University of Virginia—UVAPF Reference: WATSON-PEG.
(Continued)

*Primary Examiner* — Kevin C Sirmons
*Assistant Examiner* — Deanna K Hall
(74) *Attorney, Agent, or Firm* — Pearne & Gordon LLP

(57) ABSTRACT

A coupling apparatus includes a first component having a first non-mechanical valve, a second component having a second non-mechanical valve, and a third component having a first end for coupling with the first valve and a second end for coupling with the second valve. The third component has an elongated bore such that when the first end is coupled to the first valve and the second end is coupled to the second valve, a passageway is defined therethrough. The coupling apparatus includes a breakaway portion disposed between the third component and the second component and the first and second valves automatically close when the second and third components are separated from one another.

13 Claims, 11 Drawing Sheets

(51) Int. Cl.
   *A61M 39/26* (2006.01)
   *A61M 39/24* (2006.01)
   *A61M 39/06* (2006.01)
   *F16L 37/30* (2006.01)

(52) U.S. Cl.
   CPC ......... *A61M 39/26* (2013.01); *A61M 39/0693* (2013.01); *A61M 2039/1027* (2013.01); *A61M 2039/1077* (2013.01); *A61M 2039/2426* (2013.01); *A61M 2039/2433* (2013.01); *F04C 2270/041* (2013.01); *F16L 37/30* (2013.01); *Y10T 137/9029* (2015.04)

(56) References Cited

U.S. PATENT DOCUMENTS

| | | |
|---|---|---|
| 4,738,668 A | 4/1988 | Bellotti et al. |
| 5,316,041 A | 5/1994 | Ramacier, Jr. et al. |
| 5,494,074 A | 2/1996 | Ramacier, Jr. et al. |
| 5,820,614 A | 10/1998 | Erskine et al. |
| 6,036,171 A | 3/2000 | Weinheimer et al. |
| 6,344,033 B1 | 2/2002 | Jepson et al. |
| 6,547,284 B2 | 4/2003 | Rose et al. |
| 7,140,592 B2 | 11/2006 | Phillips |
| 7,546,857 B2 | 6/2009 | Chadbourne et al. |
| 7,766,304 B2 | 8/2010 | Phillips |
| 7,766,394 B2 | 8/2010 | Sage et al. |
| 2002/0032433 A1 | 3/2002 | Lopez |
| 2004/0124389 A1 | 7/2004 | Phillips |
| 2005/0033267 A1 | 2/2005 | Decaria |
| 2005/0090805 A1 | 4/2005 | Shaw et al. |
| 2006/0129109 A1 | 6/2006 | Shaw et al. |
| 2006/0149213 A1 | 7/2006 | Raybuck |
| 2008/0048144 A1 | 2/2008 | Lynn |
| 2008/0100061 A1 | 5/2008 | Sage et al. |
| 2008/0197626 A1 | 8/2008 | Coambs et al. |
| 2009/0163892 A1 | 6/2009 | McMichael et al. |
| 2010/0318039 A1 | 12/2010 | Hall et al. |
| 2011/0112482 A1 | 5/2011 | Redd |

FOREIGN PATENT DOCUMENTS

| | | |
|---|---|---|
| WO | 0029061 A1 | 5/2000 |
| WO | 2008054699 A2 | 5/2008 |

OTHER PUBLICATIONS

International Search Report for PCT/US2012/048515, dated Feb. 28, 2013.
Extended European Search Report for Corresponding European Application No. EP12 81 7514; Mailed Jan. 19, 2015.

\* cited by examiner

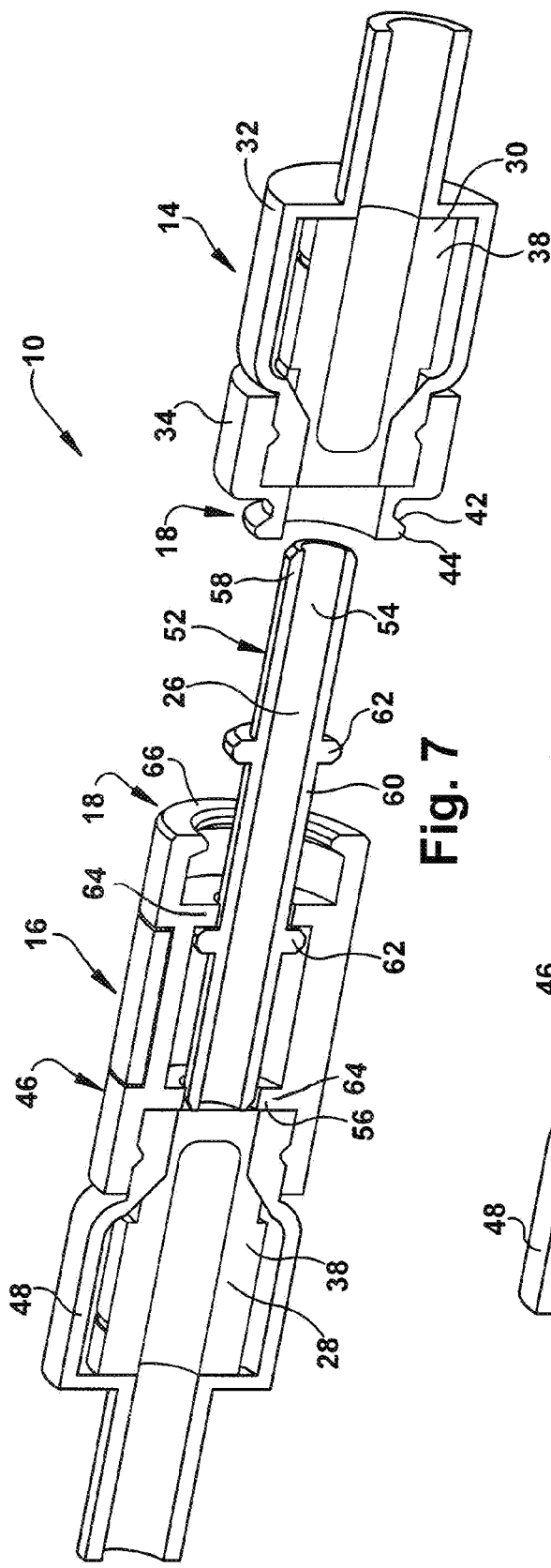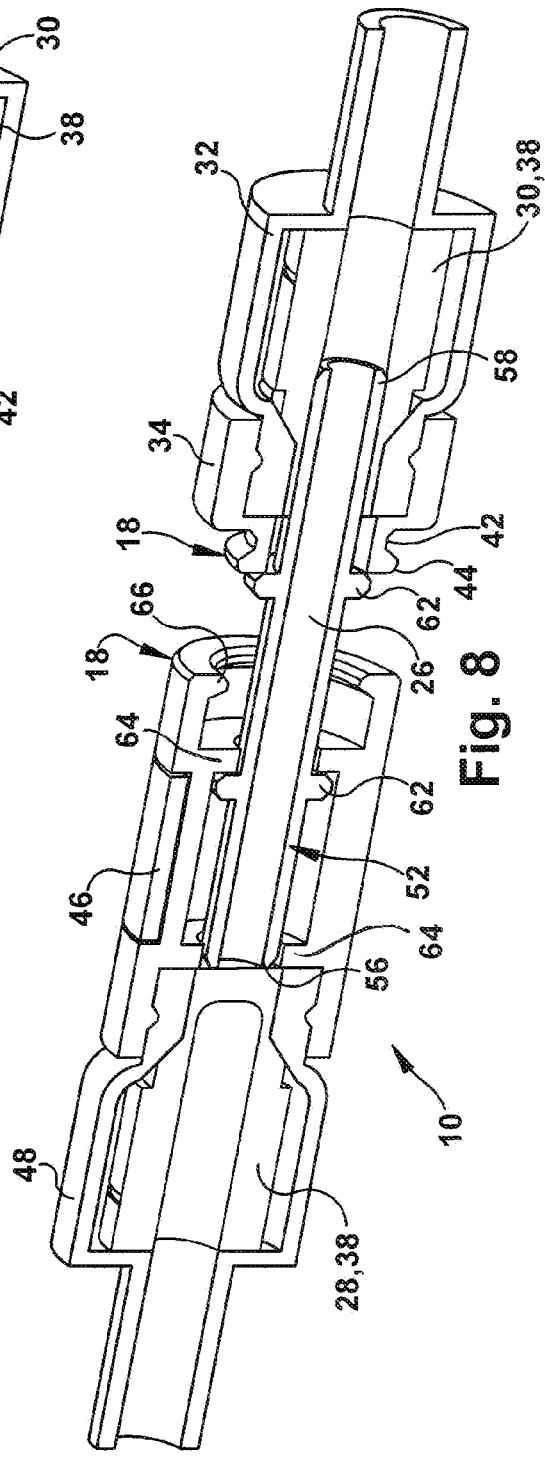
Fig. 7
Fig. 8

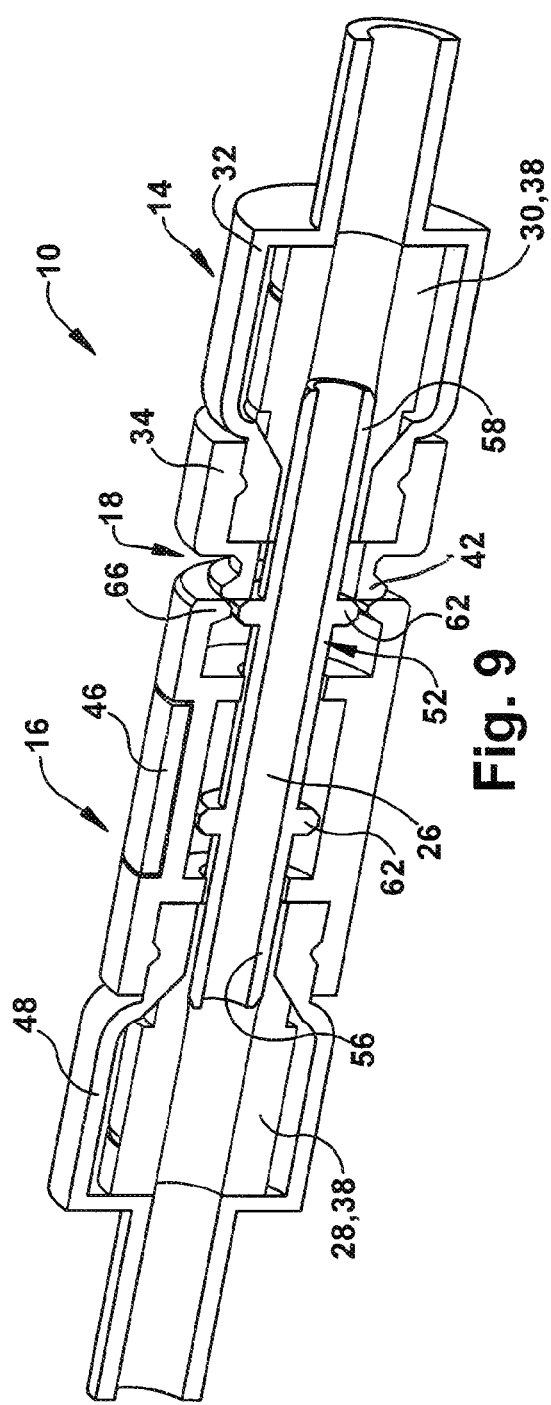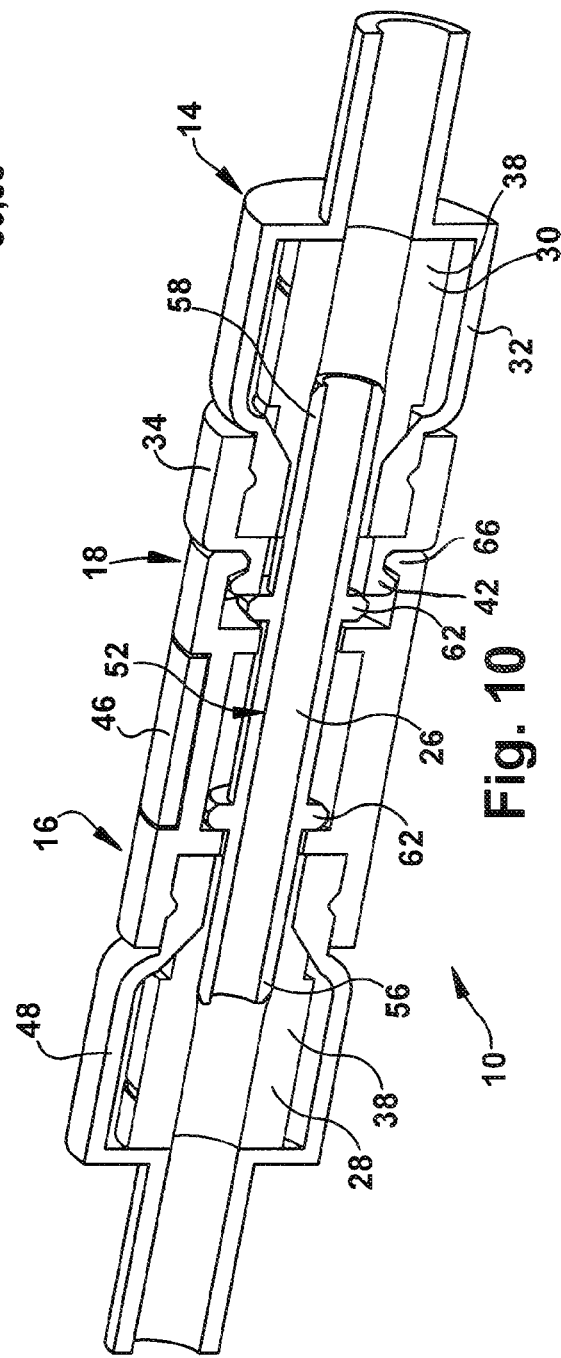

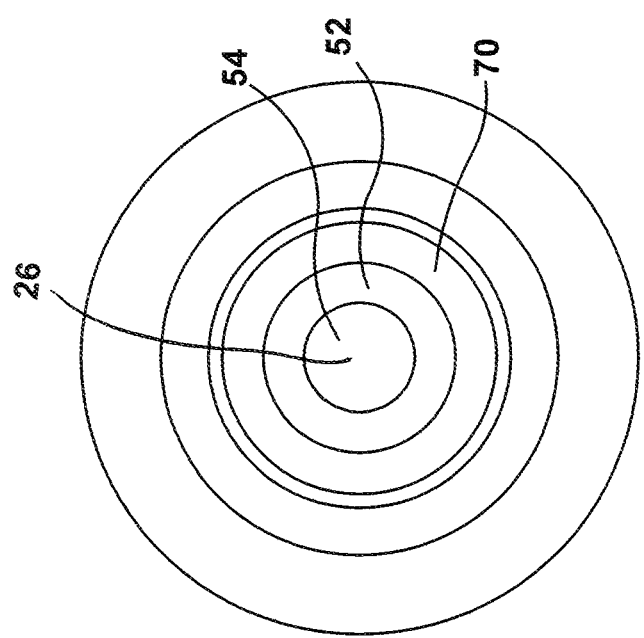

COUPLING FOR MEDICAL FLUIDS

CROSS-REFERENCE TO RELATED APPLICATIONS

This application is a continuation of U.S. application Ser. No. 13/192,630, filed Jul. 28, 2011, now U.S. Pat. No. 8,974,437, which is hereby incorporated by reference.

FIELD

This disclosure relates to a breakaway coupling for use with medical fluids. In particular, this disclosure concerns a breakaway coupling that uses valves to seal both ends of a coupling when the coupling is disconnected.

BACKGROUND

Feedset couplings are presently used in feeding tubes in order to connect a supply source with a feeding tube. Feedset couplings typically include a male adapter that mates with a female receptacle. Many such couplings do not include integrated automatic shut off valves. When a coupling becomes accidentally disconnected, such as when incidental tension is applied to the feeding system, the tube feeding can continue flowing uninterrupted from the supply source. Additionally, contents from the patient's gastrointestinal tract can backflow uninterrupted from the patient. This leads to a number of problems, such as loss of tube feeding, loss of medication, loss of time in getting the necessary daily amount of calories into a patient, compromised patient health, clean up, poor sleeping due to wetness and hunger, and potentially patient aspiration on the spilled tube feeding.

Some supply systems include alarms that signal when a feeding set is "free flowing." However, these alarm systems only work if the feeding set becomes disconnected from the pump, not if the coupling becomes disconnected. Some manufacturers have tried to prevent the feedset coupling from becoming disconnected. These devices can cause the feeding tube to be dislodged from the patient entirely, leading to additional problems.

SUMMARY

An example coupling is claimed and described herein.

BRIEF DESCRIPTION OF THE DRAWINGS

FIG. 7 is a perspective cross-sectional view of the male and female components of the first example coupling in a fully disconnected configuration;

FIG. 8 is a perspective cross-sectional view of the first example coupling in a partially engaged configuration;

FIG. 9 is a perspective cross-sectional view of the first example coupling in a further engaged configuration;

FIG. 10 is a perspective cross-sectional view of the first example coupling in a fully engaged configuration;

FIG. 20 is an end view of the example coupling of FIG. 18 showing the through passageway when in an assembled configuration.

DETAILED DESCRIPTION

Figure 1:
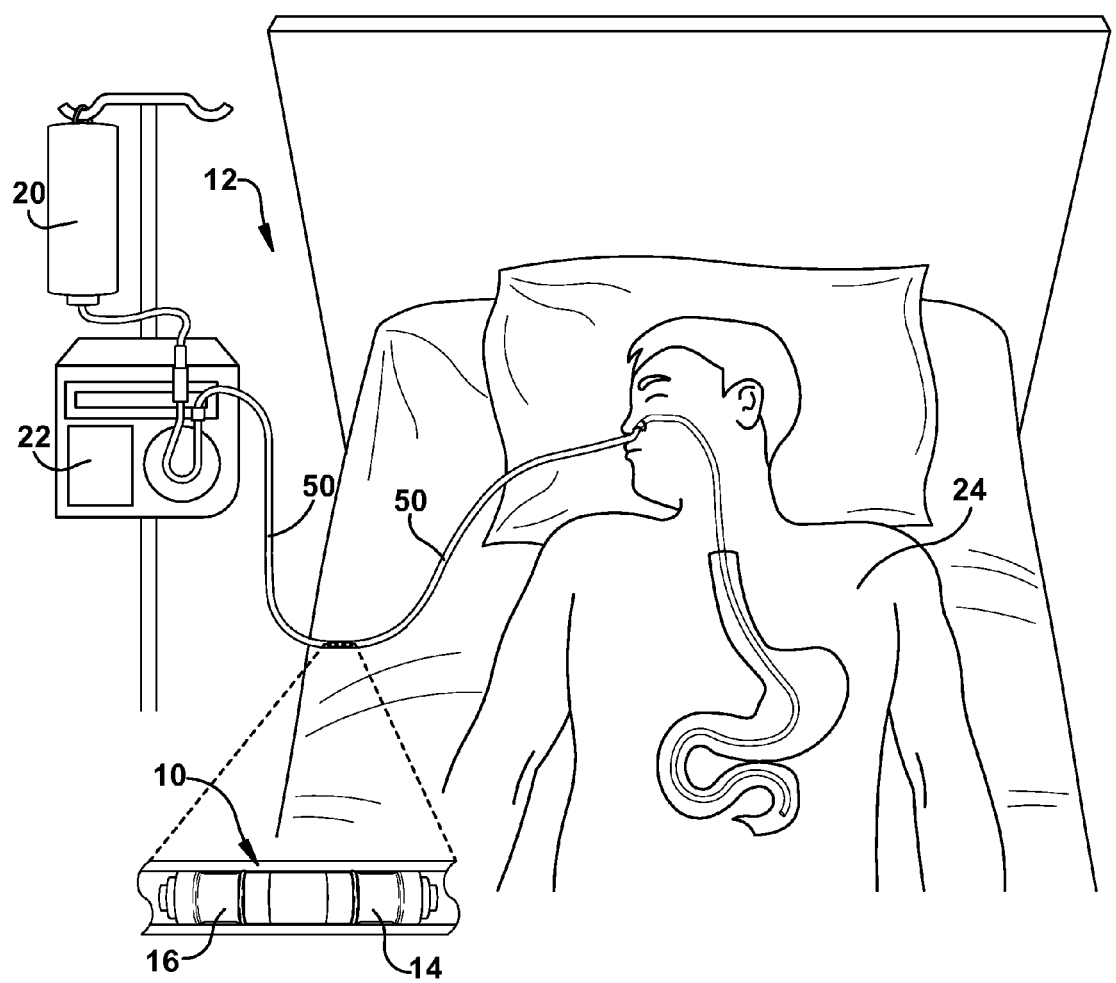
FIG. 1 depicts a first example coupling in use in connection with a feeding set.

An example coupling device 10 is an automatic shutoff breakaway coupling for a medical fluid delivery system 12. The example coupling device 10 may be used with any type of fluid delivery, such as food delivery, medication delivery, or the like. For example, the coupling 10 can be used for intravenous and arterial lines, dialysis connections, Foley catheter connections, chest tubes, or any other type of liquid, gas, or vacuum connection used for patient care. The coupling device 10 includes a female component 14 and a male component 16, with a breakaway connection 18 provided between the two components 14, 16. The housings, couplings, or other parts, as described in further detail below, can be color coded for different uses and the dimensions of the breakaway connections can be varied in order to prevent misconnections. While the description below is primarily directed to the feeding system 12 context, it should be readily recognized that the description is applicable to other systems, the invention not being limited to a particular application.

The example coupling 10 has the ability to automatically eliminate flow from both free ends of the coupling 10 when it becomes disconnected. Flow from the tube feeding supply source 20 is eliminated when the coupling 10 becomes disconnected. In addition, backflow from the patient's gastrointestinal tract 24 is eliminated. This automatic shutoff will act as an occlusion for the feeding pump 22. Since nearly all feeding pumps 22 have an occlusion sensor, this will alert a caregiver that there is a problem with the feeding system 12. Because flow is completely halted through the system 12, the caregiver will know exactly how much food has and has not been delivered. In addition, because backflow from the patient's system 24 is prevented, this assists in maintaining a patient's feeding schedule and prevents soiling of the clothes, bed and room.

The example coupling device 10 is inexpensive, disposable, small, easy to clean and quick to install. It is easy to use and the mated couplings disconnect at forces below that which would dislodge a feeding tube from a patient. The construction of the couplings 10 allows for easy sterilization. The flow path 26 through the coupling 10 is a straight path, which allows the coupling device 10 to be used with thicker fluids and prevents hemolysis of blood cells if blood is used as the transfer media. In addition, at least one example of the coupling 10 does not include any materials that could break down or corrode with repeated uses and washings, such as springs.

The amount of tension necessary to break the coupling 10 can be varied based upon the application. For example, if the coupling device 10 is to be used in delivering medication through an IV, the force needed to remove the IV might be less than the force needed to remove a feeding tube from a patient's gastrointestinal tract.

The example coupling device 10 includes a male component 16, a female component 14, and two valves 28, 30. A first valve 28 is positioned at an end of the male component 16 and a second valve 30 is positioned at the end of the female component 14. The valves 28, 30 are non-mechanical, self-closing, resilient valves. Examples of valves that are discussed herein are slit valves and duckbill valves. Any other type of non-mechanical valve may also be used.

FIG. 1 depicts the example coupling device 10 installed in a feeding system 12. The coupling 10 is positioned between the feeding pump 22 and the patient 24. An example coupling device 10 that is used for this purpose may be about two inches long. Other lengths and sizes may also be used. The size of the coupling device 10 may depend in part on the application, among other factors.

Figure 2:
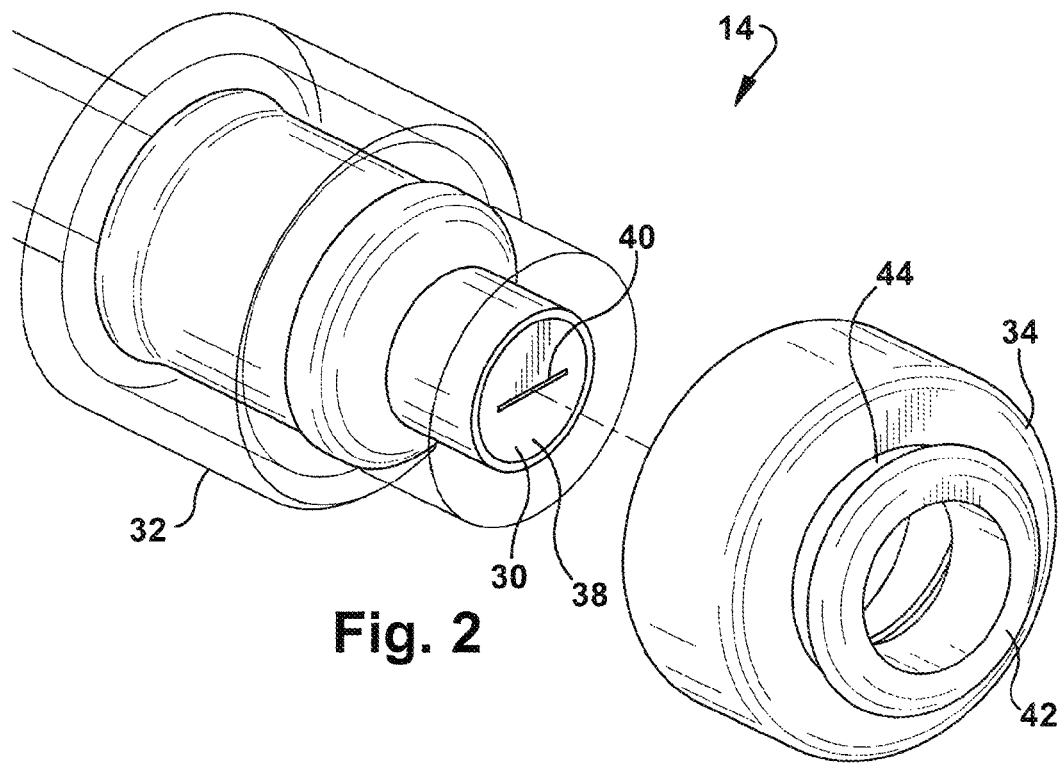
FIG. 2 is an exploded perspective view of the female components of the first example coupling.
Figure 3:
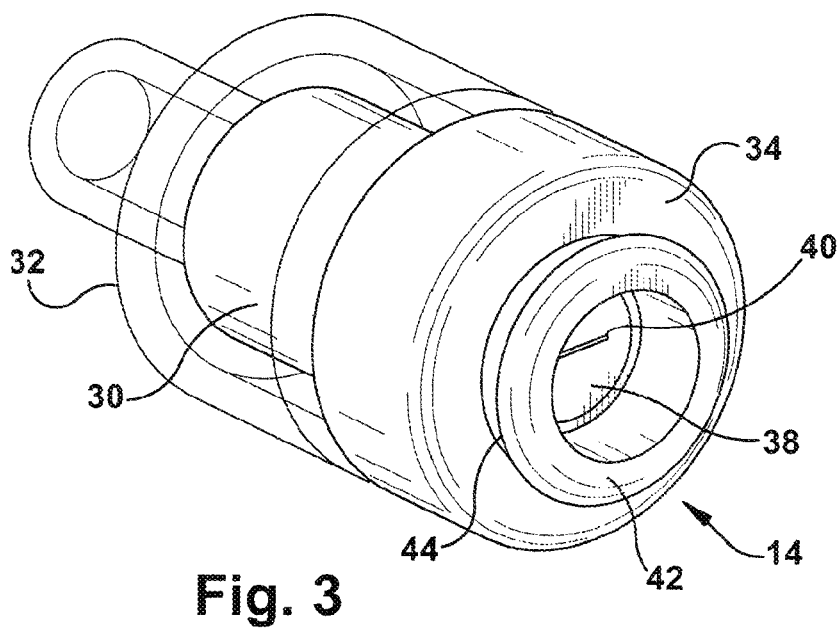
FIG. 3 is a perspective view of the female components of the example coupling of FIG. 1 in an assembled configuration.

FIGS. 2 and 3 show the female component 14 of the example coupling 10. As shown in FIG. 2, the female component 14 includes a valve 30 that is housed in a valve housing 32. A female receptacle addition 34 may be attached to the valve housing 32 via any known means, such as by adhesive or welding, among other know attachment techniques. One type of welding that may be utilized in joining these and other parts of the coupling 10 is ultrasonic welding. The female receptacle addition 34 may be molded of rigid plastic. The valve housing 32 may be formed from a polycarbonate or a copolyester and may be clear or opaque. The example valve housing 32 shown in FIGS. 2 and 3 is clear and the female receptacle addition 34 is opaque. The female receptacle addition 34 and the valve/valve housing 30, 32 are coupled together to provide a female component 14. Other types of materials may also be used for the various parts.

In FIGS. 2 and 3, a silicone slit valve 38 is shown positioned inside the valve housing 32. The slit valve 38 is positioned axially in the housing 32. The female receptacle addition 34 seats at the opening of the slit valve 38. The slit valve 38 is shown as being flush with the opening to the valve housing 32. The slit valve 38 is normally in a closed position, but can be opened by pressing an object against the slit 40 in the slit valve 38. When the object is inserted into the valve, the slit valve 38 automatically self-seals around the object. In addition, when the object is removed, the slit valve 38 automatically self seals. The slit valve 38 may be made of silicone or other materials. When an object is inserted into the slit valve 38, the valve compresses and this allows the slit 40 to open. The compressed silicone acts like a spring. When the object is removed, the compressed silicone springs back to its relaxed state and the slit 40 closes automatically.

The female receptacle addition 34 has an opening in communication with the opening of the slit valve 38 or valve 30 and serves as a guide for an object to enter the slit valve 38. The female receptacle addition 34 also has an adapter 42 at one end for coupling with another part in a breakaway manner. In particular, the adapter 42 includes a rib or lip 44 that forms a male connector that may be joined with a female receptacle 66. The rib or lip 44 extends around the opening. The rib or lip 44 may have a chamfered or rounded edge to assist in insertion into a corresponding female connector.

Figure 4:
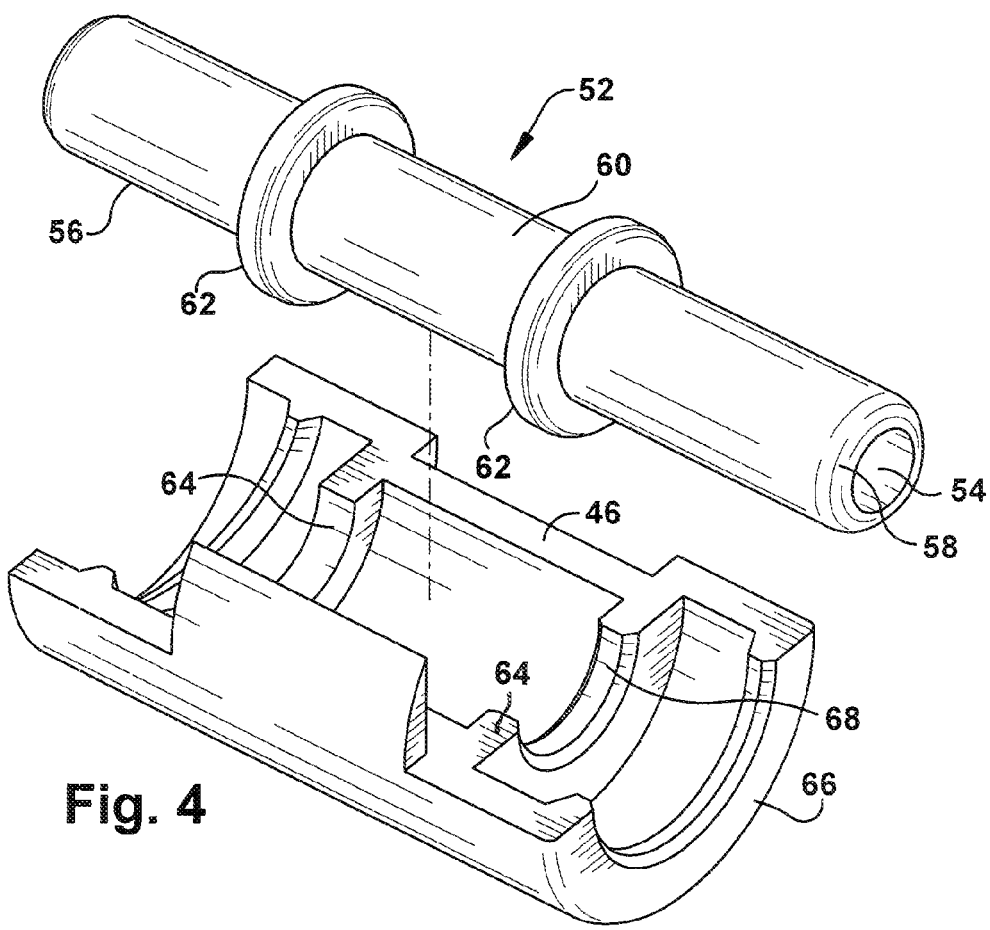
FIG. 4 is an exploded perspective view of several of the male components of the first example coupling.
Figure 5:
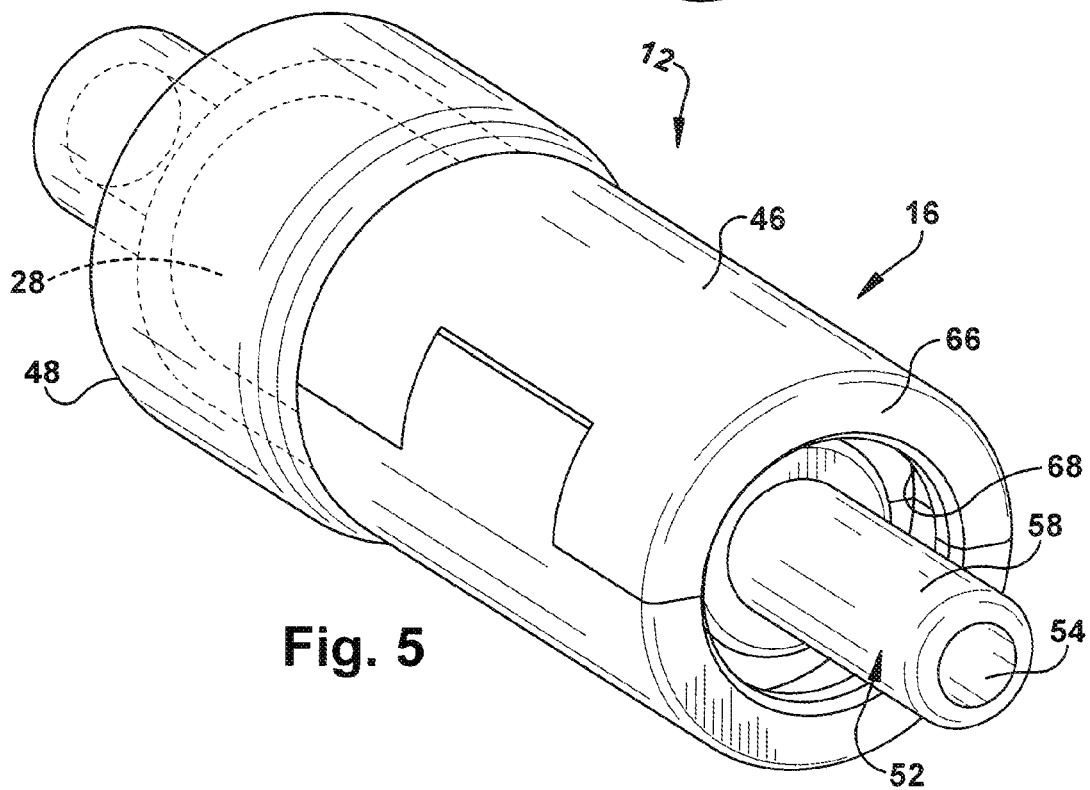
FIG. 5 is a perspective view of the male components of the example coupling of FIG. 1 in an assembled configuration.

FIGS. 4 and 5 depict parts of the male component 16 of the example coupling 10. The male component 16 includes a male housing 46 that is shown formed in two parts. The two parts may be joined together by welding, adhesive, force fit, snap fit, or other means. A slit valve 28 and valve housing 48, like those shown in FIG. 2, are coupled to one end of the male component 16 and a tube 50 of a feed system 12 may be coupled to the end of the valve housing 48. The valve housing 48 is coupled by any known means, such as welding, adhesive, or threads. The valve housing 48 may be made clear or opaque and can be a polycarbonate, a copolyester, or another material.

A floating dual male adapter 52 is elongated and has a central bore 54 that extends between the ends thereof in a single channel. The dual male adapter 52 is positioned and trapped inside the male housing 46 and has opposite end sections 56, 58 and a center section 60. Each section is separated by outwardly extending protrusions in the form of shoulders 62 that extend radially outwardly around the exterior surface of the dual male adapter 52. The shoulders 62 prevent the tips at each end 56, 58 of the dual male adapter 52 from protruding too deeply into the valves 28, 30. If the ends 56, 58 protrude too deeply into the valves 28, 30, the valves 28, 30 are unable to properly act as a spring to expel the adapter 52 during disconnection. The shoulders 62 on the dual male adapter 52 also mate with stop 64 inside the male component housing 46 to ensure each end of the dual male adapter 52 activates each valve 28, 30 equally.

The dual male adapter 52 is positioned inside the male housing 46 so that a first end 56 of the adapter 52 is in communication with the first valve 28 of the male component 16. The male housing 46 has grooves 64 for accepting one of the shoulders 62 of the dual male adapter 52 in order to trap the adapter 52 in the housing 46. The dual male adapter 52 is movable longitudinally inside the male component 16. When the dual male adapter 52 is pressed into the valve 28, the first end of the adapter enters the slit in the valve and provides a straight fluid flow pathway 26 (shown best in FIG. 9) between the interior of the male adapter 52 and an interior chamber of the valve housing 48. Other non-straight passageways could be utilized, if desired. The male component 16 of the coupling 10 is shown in FIG. 5.

Figure 11:
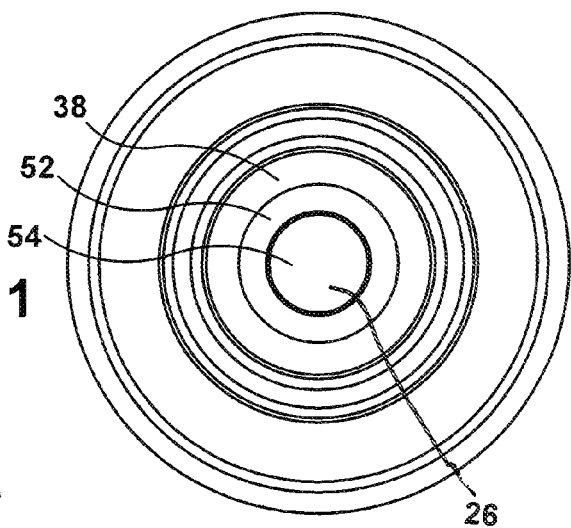
FIG. 11 is an end view of the first example coupling in a fully engaged configuration showing the through flow passageway.

FIG. 11 shows the dual male adapter 52 positioned in a slit valve 38. The dual male adapter 52 has a bore 54 creating a straight flow path 26 through the center thereof and the slit valve 38 forms a tight seal around the end of the dual male adapter 52

The male housing 46 consists of two pieces that are joined together with the dual male adapter 52 encased within it. This prevents the dual male adapter 52 from becoming detached from the assembly during normal use. Female luer lock threads are positioned at the valve end of the male housing 46 (shown in FIG. 4). These threads allow the caregiver to easily attach this assembly or remove the assembly from the functional end of a valve 28. Other types of attachment mechanisms may be used for the connection, either alone or in combination. The advantage of this assembly is that it is removable for cleaning purposes. At the other end of the male housing 46 is the female receptacle 66 of the breakaway snap feature. The design of these snaps can be changed to adjust to different breakaway forces. The design of the current snap feature enables the two ends of the coupling 10 to freely rotate without interrupting flow. This assists in avoiding tangling of the supply line 50.

As shown in FIGS. 2 and 3, the female receptacle addition 34 is bonded to the functional end of the female valve housing 32. The female component 14 contains the male fitting 44 of the breakaway snap feature that mates with the male housing 46 via the rib/lip 44. This snap feature holds the two ends of the coupling 10 together. Once enough tensile force is placed on the coupling 10 to overcome the breakaway snap force, the silicone valves 28, 30 will act as springs to expel the dual male adapter 52. This will discontinue flow from both free ends of the coupling 10.

Figure 6:
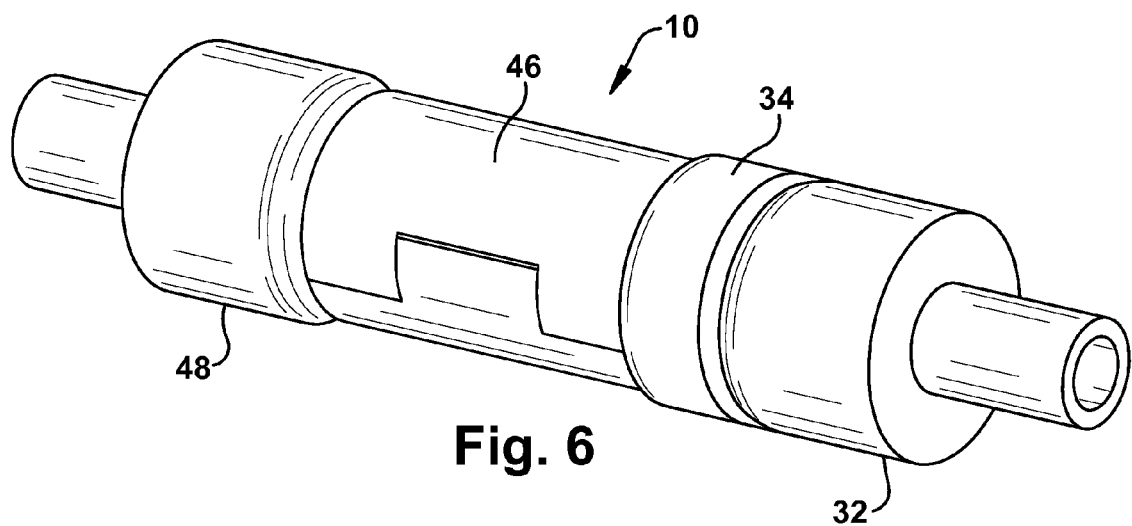
FIG. 6 is a perspective view of an assembled first example coupling that incorporates the male and female components of FIGS. 3 and 5.

FIG. 6 shows a completed coupling device 10, where the male and female components 16, 14 have been joined together. The valve housings 32, 48 are positioned at the ends of the coupling device 10 and the outer ends of the valve housings 32, 48 are used for coupling to tubing 50 in a feeding system 12, or other system. The valve housings 32, 48 may be clear and the male component housing 46 and female receptacle addition 34 may be opaque, although any of the components could be opaque or clear, if desired.

FIGS. 7-10 depict how the coupling device 10 of FIGS. 2-6 is assembled. They also show the straight flow path 26 that is created through the center of the coupling device 10. FIG. 7 shows the first valve 28 being coupled to the end of the male component 16 and the second valve 30 coupled to the female receptacle addition 34. The dual male adapter 52 is positioned inside the male component housing 46 and a shoulder 62 on the male adapter 52 is trapped inside the male housing 46 behind an inwardly protruding rib 64. The inwardly protruding rib 64 maintains the male adapter 52 in place inside the male housing 46. The opposite end 58 of the male adapter 52 is shown aligned with the female receptacle 34 on the female component 14.

FIG. 8 shows the second end 58 of the male adapter 52 being compressed against and inserted into the slit valve 38 of the female component 14. The end 58 of the male adapter 52 enters the slit 40 and is pushed entirely through the slit 40 until the opening of the adapter 52 is positioned inside a cavity inside the valve housing 32. This allows fluid to flow through the second valve 30 and through the dual male adapter 52 in a straight flow path.

FIG. 9 depicts the first end 56 of the male adapter 52 inserted into and through the first valve 28. As with the second end 58 of the male adapter 52, the first end 56 is inserted into the slit 40 in the first valve 28 until the first end 56 of the male adapter 52 enters the cavity inside the valve housing 48. In this position, the coupling device 10 is still not completely closed, although the flow path 26 has been established.

FIG. 10 depicts the male and female components 16, 14 coupled together with the fittings 42, 66 at the end of the male component 16 and female component 14 mated together. The male component 16 includes an inwardly defined rib 68 at the end thereof and the female component 14 includes an outwardly defined rib 44 at the end thereof. The flexibility of the parts allows a user to press them together until they snap into position. This connection can be broken away with the application of sufficient force. Other types of connections may also be utilized, as known by those of skill in the art.

FIGS. 12-20 depict an alternative example coupling device 10 that is similar to the device disclosed above, but includes a duckbill valve 70 instead of a slit valve 38. A duckbill valve 70 is similar to a slit valve in that it accepts an object through the opening in the valve and self seals around the object. When the object is removed from the valve, the valve automatically closes itself.

Figure 12:
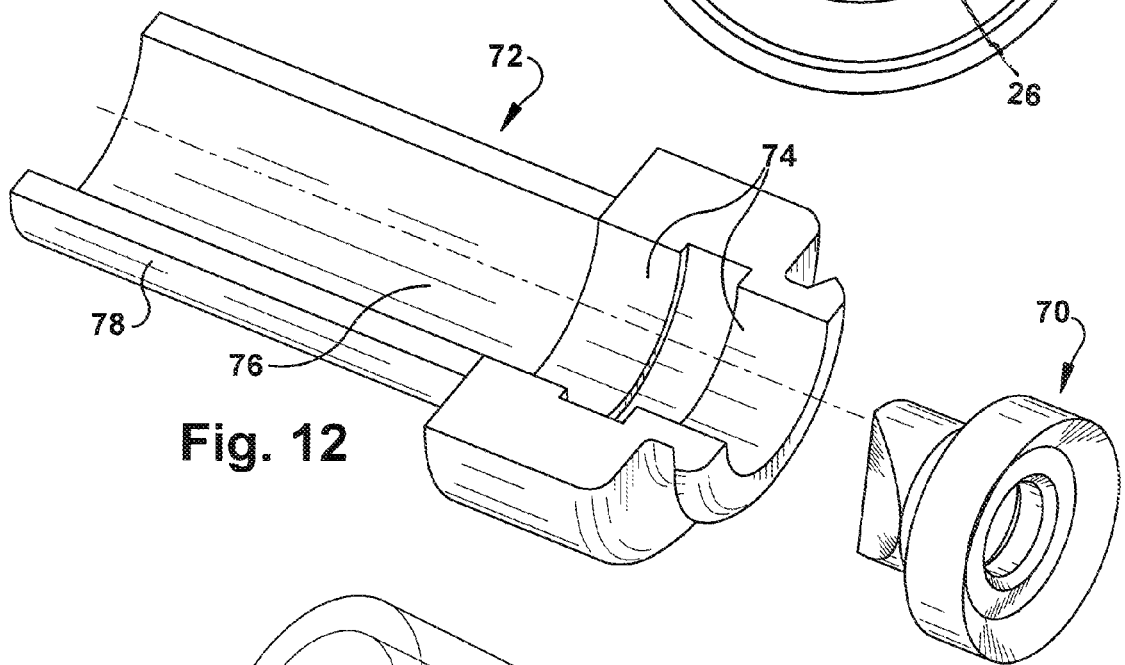
FIG. 12 is an exploded perspective view of the female components of a second example coupling.

Referring to FIG. 12, a female component 14 of the coupling device 10 is shown. The female component 14 includes a housing 72 that is formed of two parts that mate together in any known manner, such as via adhesive or welding. The housing 72 may be made of a molded rigid plastic or other material. The female housing 72 includes internally disposed ribs 74 for accepting a duckbill valve 70 and a channel 76 for accepting part of the male adapter 52. In addition, the female component 14 is provided with a channel 78 at a free end thereof for attachment to tubing 50. The duckbill valve 70 may be made of molded silicone or other materials.

Figure 13:
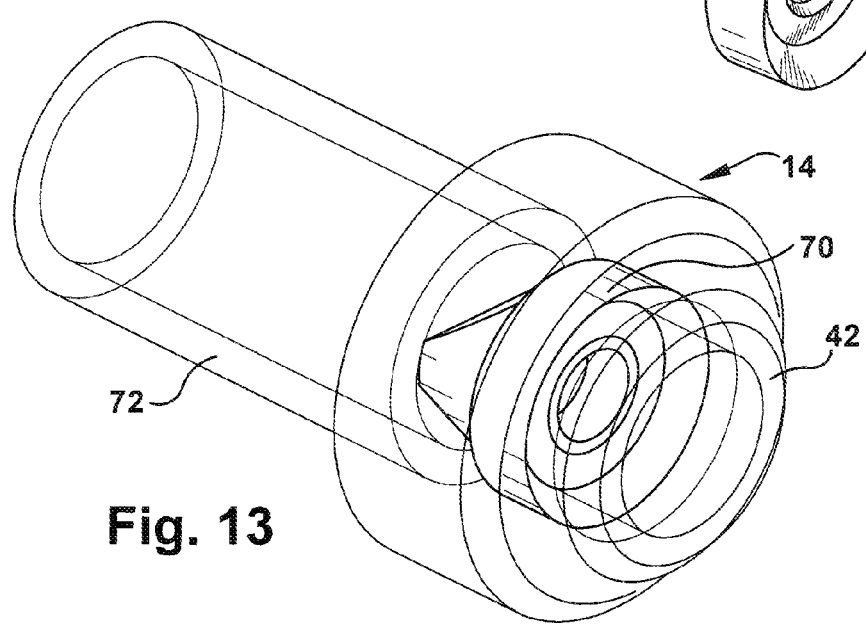
FIG. 13 is a perspective view of the female components of the second example coupling in an assembled configuration.

FIG. 13 shows the female component 14 in an assembled configuration. The duckbill valve 70 is positioned inside the housing 72 and an opening 80 is provided in the female component 14 adjacent the valve opening. The female component 14 has a fitting 42 for coupling with a male component 16 in a breakaway manner, similar to that discussed above in connection with FIGS. 2-11.

Figure 14:
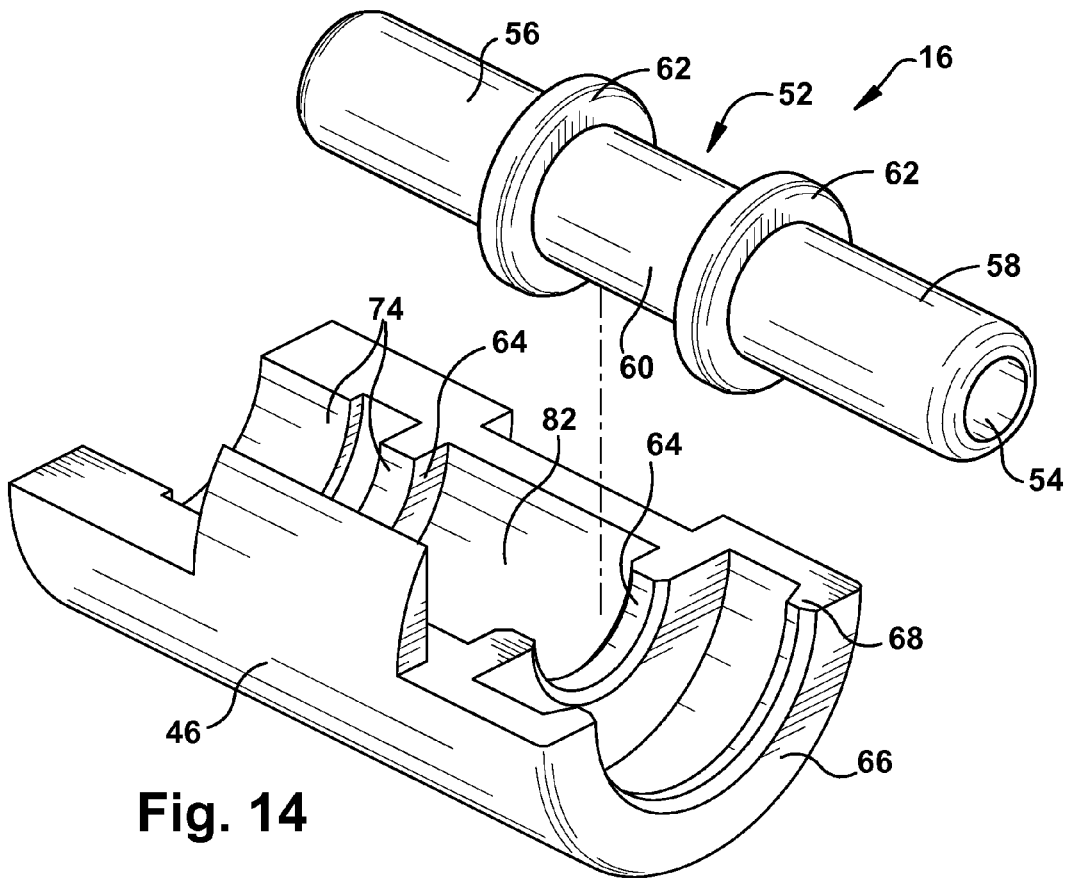
FIG. 14 is an exploded perspective view of several of the male components of the second example coupling.
Figure 15:
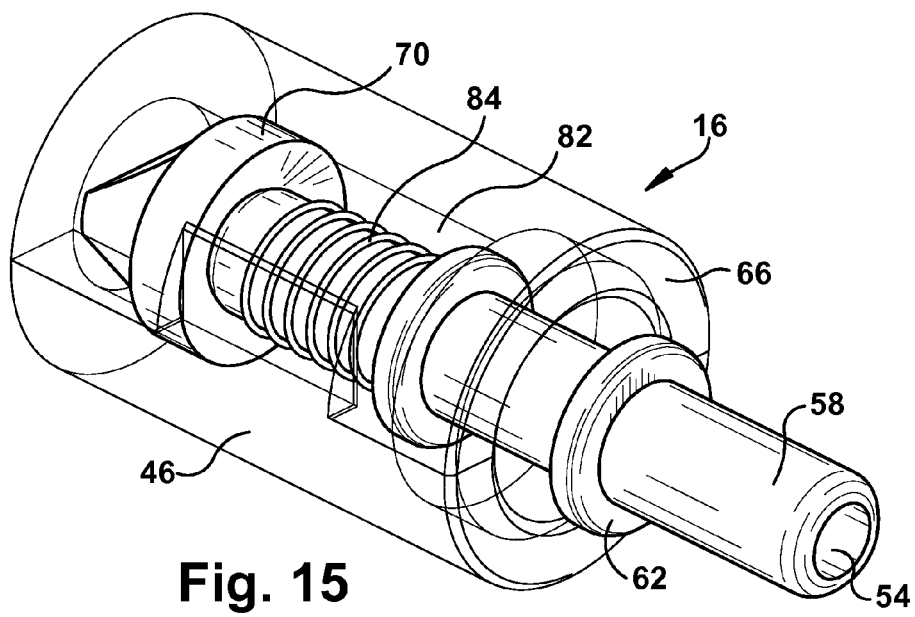
FIG. 15 is a perspective view of the male component of the second example coupling in an assembled configuration.

FIGS. 14 and 15 depict a male component 16 of the alternative example coupling 10. The male component 16 includes a male housing 46 that is formed of two halves that are joined together in any conventional manner. The housing 46 is made of a molded rigid plastic or other materials. The male housing 46 includes an interior, radially defined rib 74 for accepting a duckbill valve 70 in the interior of the housing 46. The male housing 46 also includes a chamber 82 that houses a spring 84 that is used to bias a dual male adapter 52 into an uninstalled position. The dual male adapter 52 shown is similar to that discussed above and includes two outwardly extending radial shoulders 62 and an elongated body with a passageway extending through the length thereof.

FIG. 15 shows the dual male adapter 52 and duckbill valve 70 installed in the male housing 46. The first end 56 of the dual male adapter 52 is associated with the duckbill valve 70 and the second end 58 of the adapter 52 is shown as free, but will be utilized for joining with the female component 14 of FIGS. 12/13. The first shoulder 62 on the dual male adapter 52 is positioned behind an internal rib 64 of the housing 46 in order to hold the adapter 52 in place inside the housing 46.

Figure 16:
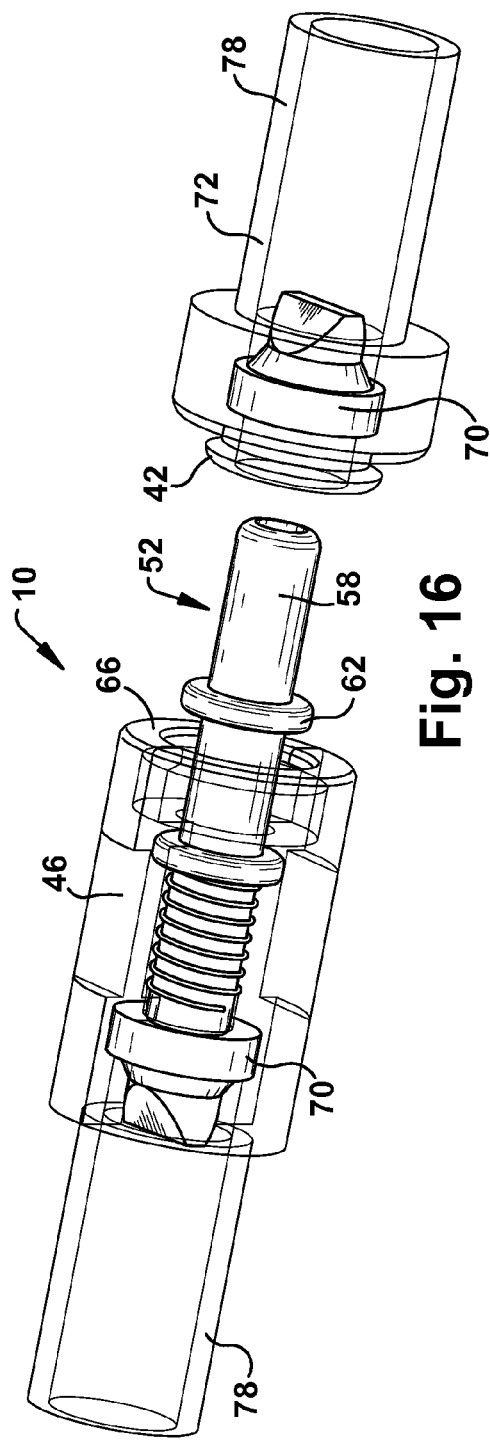
FIG. 16 is a perspective view of the male and female components of the second example coupling in an unassembled configuration.
Figure 17:
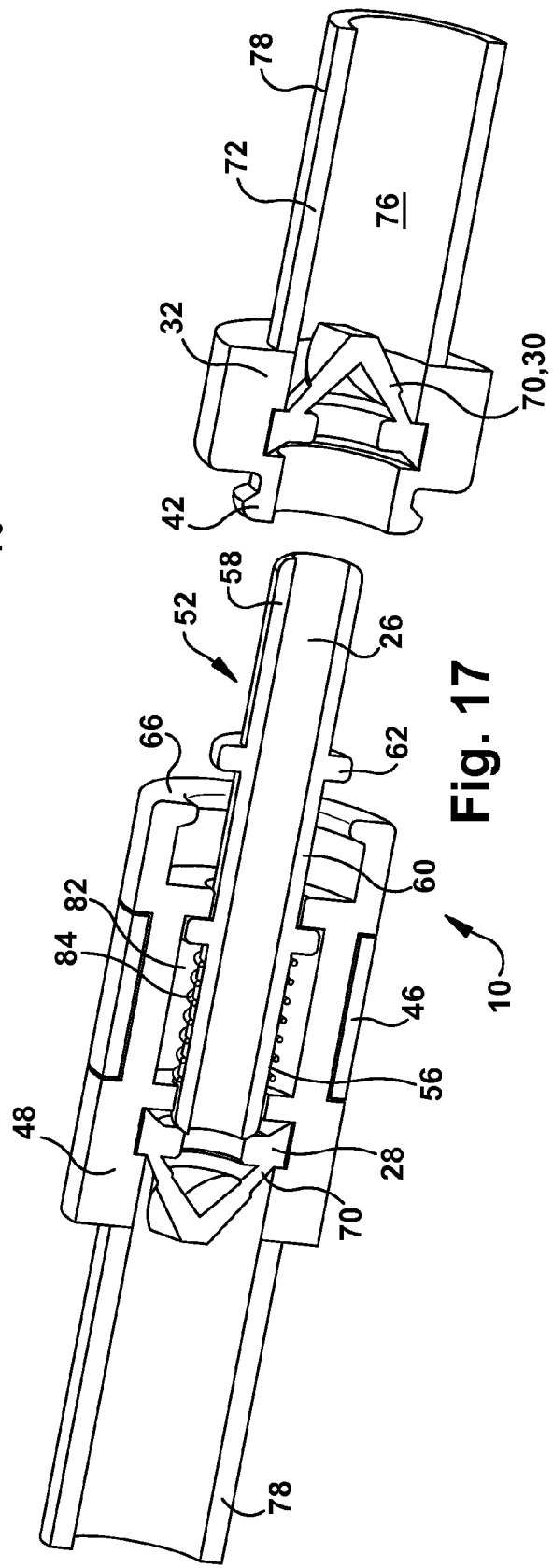
FIG. 17 is a cross-sectional perspective view of the second example coupling, as shown in FIG. 16.

FIGS. 16-19 depict the mating of the male and female components 16, 14 of the alternative example coupling device 10. FIGS. 16-17 show the male and female components 16, 14 before insertion of the dual male adapter 52 into the female component 14. The duckbill valves 70 are positioned inside the male and female components 16, 14 and the spring 84 is positioned around the first end 56 of the dual male adapter 52. The male component 16 has a female receptacle 66 at the opening thereof for coupling with a male adapter 42 defined at the end of the female component 14 in a breakaway manner. The female component 14 has an outwardly extending rib 44 for mating with the male component 16. While a snap connection is shown, other connections, such as screw threads, press fit, or the like, could also be used.

Figure 18:
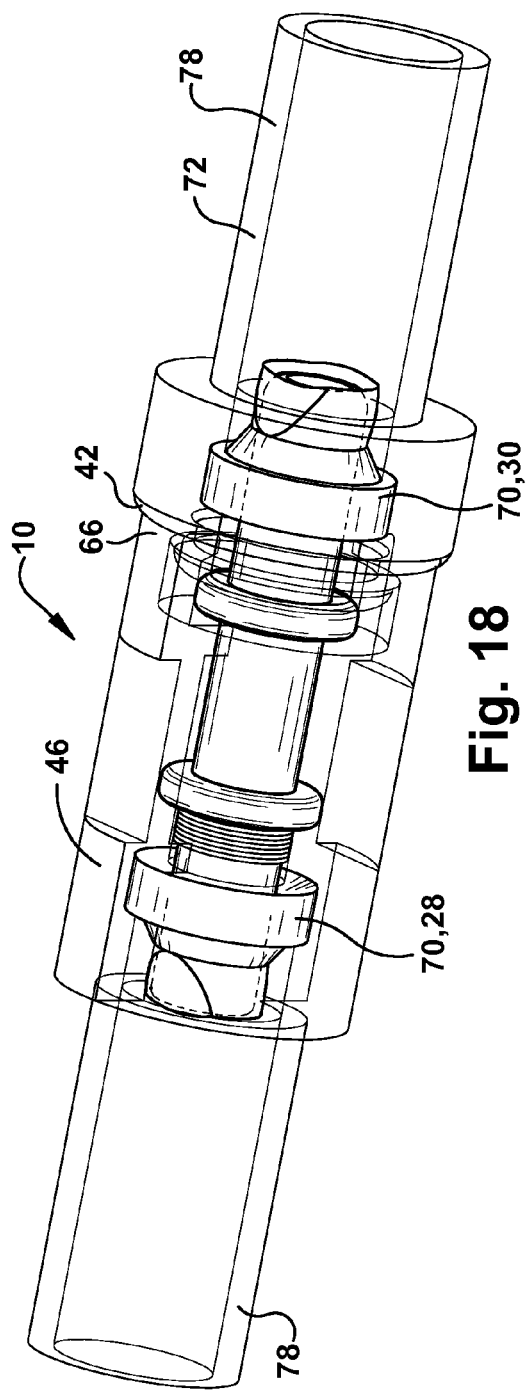
FIG. 18 is a perspective view of the second example coupling in an assembled configuration.
Figure 19:
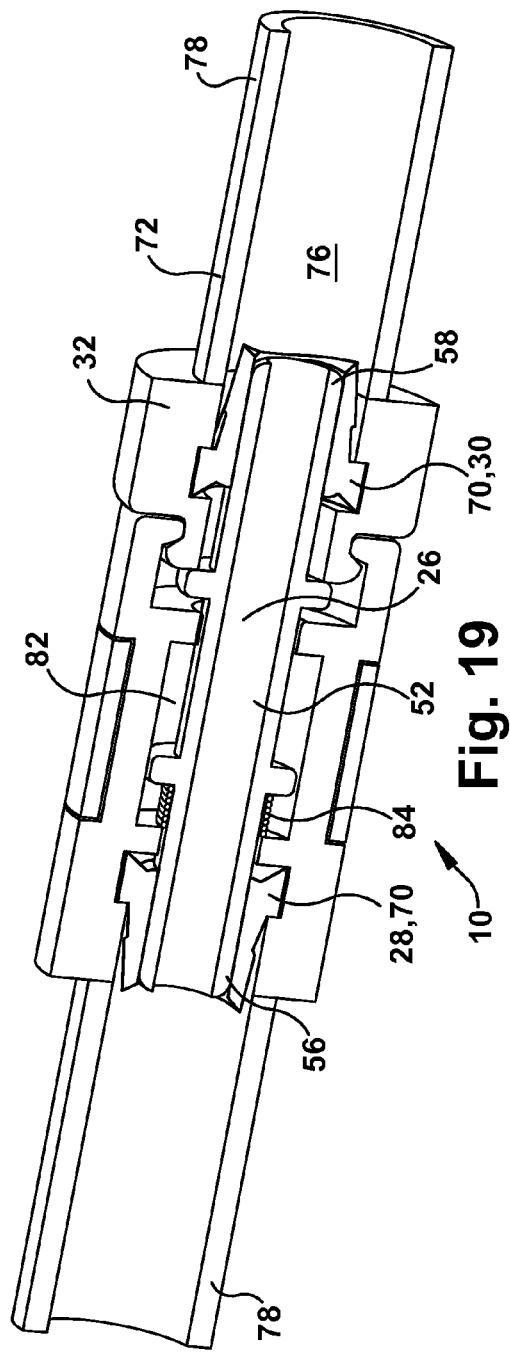
FIG. 19 is a cross-sectional perspective view of the second example coupling, as shown in FIG. 18.

FIGS. 18-19 depict the male and female components 16, 14 in a fully mated configuration. As shown, the ends 56, 58 of the dual male adapter 52 extend through both duckbill valves 70 in order to provide a straight flow path 26 through the coupling 10. Tubing 50 may be coupled at either end of the coupling 10. The male and female fittings 42, 66 are coupled together in a breakaway manner such that they can pull apart upon the exertion of sufficient force to the coupling 10. The breakaway force can be varied by varying the shape and size of the fittings 42, 66, for example. When the coupling 10 is broken away, the female component 14 separates from the male component 16 and the second end 58 of the dual male adapter 52 is removed from the female component 14 duckbill valve 70. Because of its design, the duckbill valve 70 automatically closes when the male adapter 52 is removed from the female component valve 30. Then, because the second end 58 of the dual male adapter 52 is freed, the spring 84 pushes against the shoulder 62 on the dual male adapter 52 and forces it out of the male component valve 28. This removes the first end 56 of the dual male adapter 52 from the duckbill valve 70 in the male component 16 and the duckbill valve 70 automatically closes. Thus, as is evident, when the coupling 10 is broken away, both valves 28, 30 will automatically close and no fluid may flow from the food source 20 or from the patient's system 24.

FIG. 20 shows the dual male adapter 52 positioned in a duckbill valve 70. The dual male adapter 52 has a straight flow path 26 through the center thereof and the duckbill valve 70 forms a tight seal around the end of the dual male adapter 52

The coupling apparatus comprises a first component including a first non-mechanical valve, a second component including a second non-mechanical valve, and a third component having a first end for coupling with the first valve and a second end for coupling with the second valve. The third component has an elongated bore such that when the first end is coupled to the first valve and the second end is coupled to the second valve, a passageway is defined therethrough. The passageway may have a straight flow path.

The third component may include a housing having a first half and a second half and a dual male adapter positioned inside the housing. The first component includes a first housing and the first valve, and the second component includes a second housing and the second valve. At least one of the first and second housings has a fitting for fixedly axially coupling with the third component housing.

At least one of the first and second components includes a female receptacle for mating with the dual male adapter. The first and second valves are resilient, self-sealing members. Each of the resilient sealing members has a slit in one end thereof that extends through the resilient member and allows the ends of the third component to penetrate the respective sealing member. The first and second valves are duckbill valves or slit valves.

The dual male adapter is elongated and the first end is for inserting into and through the first valve. The second end of the dual male adapter is for inserting into and through the second valve. The dual male adapter includes a first protrusion and a second protrusion on an exterior surface thereof. The protrusions are for mating with surfaces defined in at least the third component housing for maintaining at least part of the dual male adapter inside the third component housing. The dual male adapter is movable in the third component housing.

The third component housing includes a snap surface and the housing of the adjoining component has a snap surface. The snap surfaces, when joined together, can be broken away from one another to release the third component from the adjoining component. The first component may be secured to the third component with welding, adhesive, or a fitting. The second component may be secured to the third component with a fitting.

The third component includes a third housing having a first half and a second half and a dual male adapter positioned inside the third housing. The first component is integral with the third component, and the second component includes a second housing having a first half and a second half and the second valve. The second housing has a fitting for fixedly axially coupling with the third component housing. The fitting is a breakaway fitting, the first and second valves are duckbill valves. A coil spring is positioned inside the third component housing and biases the dual male adapter into an uninstalled position.

In another example, a coupling apparatus comprises a first component having a first non-mechanical valve, a second component having a second non-mechanical valve, and a third component having a first end for coupling with the first valve and a second end for coupling with the second valve to establish fluid flow therethrough. The third component is detachable from one or more of the first and second components upon the exertion of sufficient force. When one or both of the first and second components are detached from the third component, the first and second valves automatically close.

Fluid flow therethrough may be along a centrally disposed, axial flow path. The first and second valves are duckbill valves or slit valves.

In another example, an automatic shutoff breakaway component for a medical fluid device comprises a male component attachable to tubing for receiving a fluid and a dual male adapter coupled to the male component. The dual male adapter has a first end and a second end. The automatic shutoff breakaway component also includes a valve coupled to the male component 16 and to one end of the dual male adapter. The valve is positioned between the tubing and the dual male adapter.

The valve may be integral with the male component and the male component has a fitting for coupling with another part. A female component may be coupled with the male component. The female component has an opening for receiving the other end of the dual male adapter and includes a second valve for mating with the dual male adapter end.

The term "substantially," if used herein, is a term of estimation.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. A coupling apparatus comprising;
a first housing;
a second housing;
a non-mechanical valve; and
a component having a first end and a second end;
wherein:
the first housing and the second housing are coupled to, and separable from, each other;

the second housing houses the non-mechanical valve and the component;

at least one of the first end of the component or the second end of the component is for coupling with the non-mechanical valve;

the component has an elongated bore such that when the first end of the component or the second end of the component is coupled to the non-mechanical valve, a passageway is defined therethrough;

the component comprises a dual male adapter and at least one of the first and second housings includes a female receptacle for mating with the dual male adapter; and the dual male adapter is elongated and at least one of the first end of the component or the second end of the component is for inserting into, and through, the non-mechanical valve.

2. The coupling apparatus of claim 1, wherein the first housing has a first fitting on at least one end thereof and the second housing has a second fitting on at least one end thereof, and the first housing is coupled to the second housing via the joining of the first and second fittings.

3. The coupling apparatus of claim 2, wherein the dual male adapter is positioned inside the first and the second housings, and the first and second fittings are for axially coupling the first and second housings together.

4. The coupling apparatus of claim 1, wherein the first housing is removable from and rejoinable with the second housing.

5. The coupling of claim 1, wherein the first housing is removable from the second housing via the application of a prescribed level of force.

6. The coupling apparatus of claim 1, wherein the non-mechanical valve is a resilient, self-sealing member.

7. The coupling apparatus of claim 6, wherein the resilient, self-sealing member has a slit in one end thereof that extends therethrough and allows at least one of the first end of the component or the second end of the component to penetrate the respective sealing member.

8. The coupling apparatus of claim 1, wherein the non-mechanical valve is a duckbill valve or a slit valve.

9. The coupling apparatus of claim 1, wherein the passageway has a straight flow path that is substantially free from voids that could allow stagnation of any part of a fluid traveling through the passageway.

10. The coupling apparatus of claim 1, wherein the component is maintained in the second housing when the first and second housings are separated from one another.

11. A coupling apparatus comprising;
a first housing;
a second housing;
a non-mechanical valve; and
a component having a first end and a second end;
wherein:
the first housing and the second housing are coupled to, and separable from, each other;
the second housing houses the non-mechanical valve and the component;
at least one of the first end of the component or the second end of the component is for coupling with the non-mechanical valve;
the component has an elongated bore such that when the first end of the component or the second end of the component is coupled to the non-mechanical valve, a passageway is defined therethrough;
the component comprises a dual male adapter and at least one of the first and second housings includes a female receptacle for mating with the dual male adapter; and
the dual male adapter includes a first protrusion and a second protrusion on an exterior surface thereof, said protrusions for mating with surfaces defined in the second housing for retaining the dual male adapter inside the second housing, and the dual male adapter is axially movable in the second housing.

12. A coupling apparatus comprising;
a first housing;
a second housing;
a non-mechanical valve; and
a component having a first end and a second end;
wherein:
the first housing and the second housing are coupled to, and separable from, each other;
the second housing houses the non-mechanical valve and the component;
at least one of the first end of the component or the second end of the component is for coupling with the non-mechanical valve;
the component has an elongated bore such that when the first end of the component or the second end of the component is coupled to the non-mechanical valve, a passageway is defined therethrough;
the component comprises a dual male adapter and at least one of the first and second housings includes a female receptacle for mating with the dual male adapter; and
the component is axially movable in the second housing, such that:
  (i) when the first housing and the second housing are coupled to each other at least one of the first end of the component or the second end of the component is inserted into, and through, the non-mechanical valve; and
  (ii) when the first and second housings are separated from one another (a) the component is maintained in the second housing, (b) the component moves axially, and (c) the at least one of the first end of the component or the second end of the component is withdrawn from the non-mechanical valve.

13. The coupling apparatus of claim 12, wherein the component includes a first protrusion and a second protrusion on an exterior surface thereof, said protrusions for mating with surfaces defined in the second housing for retaining the component inside the second housing.

* * * * *